United States Patent [19]

Giesecke et al.

[11] 4,163,857
[45] Aug. 7, 1979

[54] PARABANIC ACID AMINALS

[75] Inventors: Henning Giesecke, Cologne; Jürgen Hocker, Bergisch Gladbach; Rudolf Merten, Leverkusen, all of Fed. Rep. of Germany

[73] Assignee: Bayer Aktiengesellschaft, Leverkusen, Fed. Rep. of Germany

[21] Appl. No.: 819,870

[22] Filed: Jul. 28, 1977

Related U.S. Application Data

[63] Continuation-in-part of Ser. No. 804,607, Jun. 8, 1977, abandoned.

[30] Foreign Application Priority Data

Jun. 9, 1976 [DE] Fed. Rep. of Germany ....... 2625722

[51] Int. Cl.² ............................................. C07D 233/02
[52] U.S. Cl. ................................. 548/318; 424/273 R
[58] Field of Search ................................ 548/309, 318

[56] References Cited

PUBLICATIONS

Hocker et al., I Chem. Abst. 1972, vol. 76, No. 14435b.
Hocker et al., II Justus Liebigs Ann. Chem. 1971, vol. 751, pp. 145–154.
Regitz et al., I Chem. Abst. 1970, vol. 73, No. 77141m.
Regitz et al., II Chem. Abstr. 1971, vol. 75, No. 98495m.
Regitz et al., III Justus Liebigs Ann. Chem. 1971, vol. 748, pp. 1–19.
Schoessler et al., I Chem. Abst. 1974, vol. 81, No. 63550x.
Schössler et al., II Chem. Ber. 1974, vol. 107, pp. 1931–1948.
Winberg et al., J. Amer. Chem. Soc. 1965, vol. 87, pp. 2776–2777.

*Primary Examiner*—Alan L. Rotman
*Attorney, Agent, or Firm*—Connolly and Hutz

[57] ABSTRACT

Parabanic acid aminals of the formula

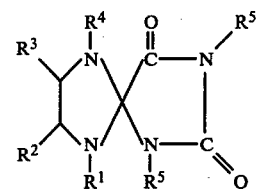

wherein $R^1$ is

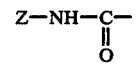

wherein Z is selected from the group consisting of an aliphatic radical having 1–20 carbon atoms, an aromatic radical having 6–14 carbon atoms and an aliphatic-aromatic radical having 7–20 carbon atoms;

$R^2$ and $R^3$ may be the same or different and each is selected from the group consisting of hydrogen, an aliphatic radical having 1–20 carbon atoms, an aromatic radical having 6–14 carbon atoms and an aliphatic-aromatic having 7–20 carbon atoms; $R^4$ is hydrogen or

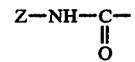

with Z being as defined above; and $R^5$ is the same as Z.

10 Claims, No Drawings

PARABANIC ACID AMINALS

This is a continuation-in-part of copending application Ser. No. 804,607 filed June 8, 1977, now abandoned.

This invention relates to new parabanic acid aminals and to a process for the production thereof.

These new compounds correspond to the following general formula:

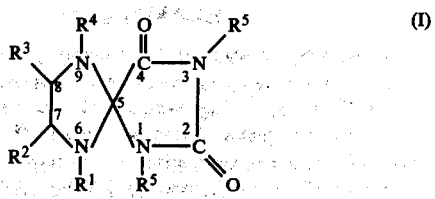

wherein
- $R^1$ represents an optionally substituted aliphatic, aliphatic-aromatic or aromatic carbamoyl radical;
- $R^2$ and $R^3$, which may be the same or different, each represents a hydrogen atom or an optionally substituted aliphatic, aliphatic-aromatic, aromatic radical; or together form a ring;
- $R^4$ represents a hydrogen atom or an optionally substituted aliphatic, aliphatic-aromatic or aromatic carbamoyl radical; and
- $R^5$ represents an optionally substituted aliphatic, aliphatic-aromatic or aromatic radical.

An alternative method for numbering the compounds of this invention is

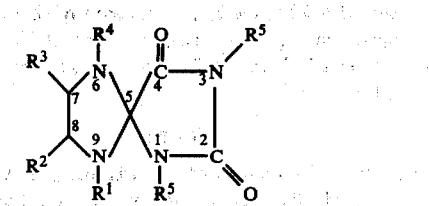

The optionally substituted aliphatic radicals preferably contain from 1 to 20 carbon atoms, these radicals may contain up to 2 double bonds or 1 triple bond. The optionally substituted cycloaliphatic radicals preferably contain from 5 to 12, more preferably 5 or 6 carbon atoms in the ring and are, of course, also regarded as aliphatic radicals in the context of the present invention.

The optionally substituted aromatic radicals are preferably contain from 6 to 14 carbon atoms, more preferably from 6 to 10 carbon atoms, more especially 6 carbon atoms in the ring system. In the case of the phenyl radical, it may optionally be attached to another aryl radical through an oxygen or sulphur atom.

The aliphatic-aromatic radicals preferably contain from 7 to 20 carbon atoms.

Carbamoyl radicals are radicals corresponding to the following structure:

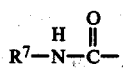

wherein
$R^7$ has the meaning of $R^5$ and represents an optionally substituted aliphatic radical, preferably having from 1 to 16 carbon atoms, an aliphatic-aromatic radical preferably having from 7 to 20 carbon atoms or an aromatic radical, preferably having from 6 to 14 carbon atoms, with the above meaning.

Substituents on the above-mentioned aromatic and aliphatic radicals are, for example, $C_6$–$C_{16}$ aryl (preferably phenyl), CN, $NO_2$, alkyl mercapto and alkoxy groups preferably containing from 1 to 4 carbon atoms, carboxylic ester groups, preferably those with lower aliphatic alcohols, preferably containing from 1 to 8 and more especially from 1 to 4 carbon atoms, and also the disubstituted amino group, preferably substituted by lower aliphatic radicals (preferably having from 1 to 4 carbon atoms), halogen (preferably fluorine, chlorine, bromine), lower haloalkyl radicals (preferably having from 1 to 4 carbon atoms, the halogen preferably being fluorine and/or chlorine) and, in the case of the aromatic radicals, also lower alkyl groups, preferably containing from 1 to 4 carbon atoms.

The above-mentioned structure of the inventive compounds was confirmed by elemental analysis, mass spectra, $^1$H-NMR-spectra and $^{13}$C-NMR-spectra. The IR-spectra show the carbonyl bands typical of parabanic acids at from 1710 to 1740 cm$^{-1}$ (strong) and at from 1770 to 1800 cm$^{-1}$ (weak), in addition to urea carbonyl bands at from 1630 to 1700 cm$^{-1}$ (strong).

The present invention also relates to a process for preparing the parabanic acid aminals according to the present invention wherein 2-imidazolines corresponding to the following general formula:

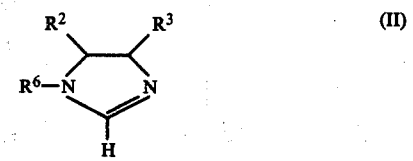

wherein
$R^2$ and $R^3$ are as defined above; and
$R^6$ has the same meanings as $R^4$ above, are reacted with organic monoisocyanates.

The process according to the present invention for producing the new parabanic acid aminals is generally carried out as follows:

The starting substances may be used in such quantities that from 0.5 to 10 moles, preferably from 3 to 4 moles, of isocyanate groups are available per mole of 2-imidazoline.

In general, it is best to carry out the reaction in a solvent or diluent, in which case the starting materials may either be dissolved or even simply suspended. It is, of course, also possible to carry out the reaction in the absence of a solvent or diluent. Solvents suitable for use in the process according to the present invention are compounds which are inert to NCO-groups, for example aromatic hydrocarbons, chlorinated aromatic hydrocarbons, benzonitrile, aliphatic hydrocarbons, esters and ketones. Particularly suitable solvents are toluene, xylene, mesitylene, chlorobenzene, dichlorobenzene, N-methyl pyrrolidone, dimethyl formamide, dimethyl acetamide, hexamethyl phosphoric acid triamide, tetramethyl urea, nitromethane and nitrobenzene.

The reaction according to the present invention is carried out at temperatures of from −20° to +250° C. It is preferably carried out at temperatures of from 30° to 200° C., more especially at temperatures of from 80° to 160° C.

It is generally best to carry out the reaction in the absence of moisture.

It may be advantageous, especially in cases where readily volatile isocyanates are used, to carry out the reaction under pressure, for example at an excess pressure of from 0.5 to 10 atmospheres, preferably from 0.5 to 5 atmospheres.

In order to accelerate the reaction and to suppress secondary reactions, it may be advantageous to add acidic or basic catalysts, especially the catalysts normally used in isocyanate chemistry, such as metal alcoholates and tertiary amines.

The reaction according to the present invention is exemplified by the following reaction equation:

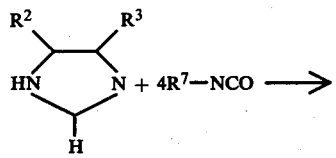

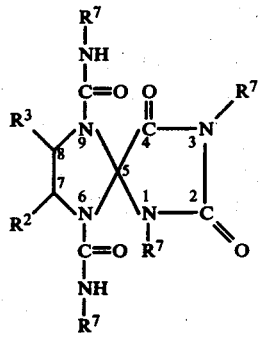

The following $\Delta^2$-imidazolines are preferred for carrying out the process according to the present invention:

2-imidazoline
4-methyl-2-imidazoline
4-ethyl-2-imidazoline
4-cyclohexyl-2-imidazoline
4-phenyl-2-imidazoline
4-(p-chlorophenyl)-2-imidazoline
4,5-dimethyl-2-imidazoline
5-ethyl-4-methyl-2-imidazoline
5-methyl-4-phenyl-2-imidazoline    hexahydrobenzimidazole
1-(methylcarbamoyl)-2-imidazoline
1-(n-propylcarbamoyl)-2-imidazoline
1-(cyclohexylcarbamoyl)-2-imidazoline
1-(phenylcarbamoyl)-2-imidazoline
1-(3,4-dichlorophenylcarbamoyl)-2-imidazoline
1-(p-nitrophenylcarbamoyl)-2-imidazoline
1-(methylcarbamoyl)-4-methyl-2-imidazoline
1-(phenylcarbamoyl)-hexahydrobenzimidazole
1-(p-tolylcarbamoyl)-5-(naphthyl)-1-2-imidazoline Organic isocyanates preferably used for carrying out the process according to the present invention are aliphatic monoisocyanates having from 2 to 21 carbon atoms or aromatic monoisocyanates having from 7 to 15 carbon atoms.

It is particularly preferred to use methyl, ethyl, allyl, n-propyl, n-butyl, iso-butyl, tert.-butyl, n-amyl, dodecyl, olely, stearyl, cyclohexyl, 1-chloro-2-ethyl, methoxy methyl, 1-cyano-3-propyl, phenyl, o-tolyl, p-tolyl, benzyl, m-tolyl, 4-chlorophenyl, 3,4-dichlorophenyl, 2-nitrophenyl, 3-cyanophenyl, 4-methoxyphenyl and 1-naphthyl isocyanate.

The compounds according to the present invention may be used as auxiliaries for textiles and rubber and also as pharmaceuticals and plant protection agents. For example the compounds of the present invention are active against Fusicladium or apple seedlings. They may be applied to the seedlings from solutions or suspensions at concentrations of from 0,001 to 1 percent by weight.

EXAMPLE 1

7.0 parts by weight, of 2-imidazoline and 50 parts by weight of cyclohexyl isocyanate are stirred for 25 hours at 110° C. in 25 parts by weight, of toluene. On cooling, a deposit is precipitated and is filtered off under suction and washed with ether, giving 38.3 parts by weight, of the parabanic acid derivative 1,3-dicyclohexyl-6,9-bis-cyclohexyl carbamoyl-2,4-dioxo-1,3,6,9-tetraaza-spiro [4.4]-nonane, melting at 188°–190° C.

|  |  | C | H | N |
|---|---|---|---|---|
| $C_{31}H_{50}N_6O_4$ | Calculated | 65.23 | 8.83 | 14.72 |
|  | Observed | 65.0 | 9.0 | 14.9 |

EXAMPLE 2

2.8 parts by weight, of 2-imidazoline and 9 parts, by weight, of methyl isocyanate are heated for 50 hours at 150° C. in a sealed tube. On cooling, a resin-like product is formed and is rubbed with cyclohexane, giving 2.5 parts, by weight, of the parabanic acid derivative 1,3-dimethyl-6,9-bis-methyl carbamoyl-2,4-dioxo-1,3,6,9-tetraaza-spiro [4.4]-nonane, melting at 272° C. (decomposition). IR (KBr): 1776 cm$^{-1}$, 1721 cm$^{-1}$, 1647 cm$^{-1}$ (C=O)

EXAMPLE 3

3.5 parts by weight of 2-imidazoline and 16.6 parts by weight, of allyl isocyanate are stirred for 26 hours at 110° C. in 10 parts by weight, of toluene. On cooling, a colourless deposit is precipitated and is filtered off under suction and washed with toluene, giving 3.8 parts by weight, of the parabanic acid derivative: 1,3-diallyl-6,9-bis-allyl carbamoyl-2,4-dioxo-1,3,6,9-tetraaza-spiro [4.4]-nonane, melting at 171° C. MS: Mole peak 402

EXAMPLE 4

47.6 parts by weight, of phenyl isocyanate are added dropwise over a period of 1 hour at 100° C. to 7 parts by weight, of 2-imidazoline in 25 parts by weight, of chlorobenzene, followed by stirring for 3 hours at 130° C. On cooling, a deposit is precipitated which is filtered off under suction and washed with chlorobenzene, giving 23 parts, by weight, of the parabanic acid derivative: 2,4-dioxo-1,3-diphenyl-6-phenyl carbamoyl-1,3,6,9-tetraaza-spiro [4.4]-nonane, melting at 248° C. Molecular weight (osmometric): Found 431, calculated 427.5

EXAMPLE 5

9.45 parts by weight, of 1-phenyl carbamoyl-2-imidazoline and 11.9 parts by weight, of phenyl isocyanate are heated for 1 hour at 140° C. in 20 parts by weight, of xylene. On cooling, a deposit is precipitated which is filtered off under suction and washed with a little toluene, giving 16.7 parts by weight, of the parabanic acid derivative: 2,4-dioxo-1,3-diphenyl-6-phenyl carbamoyl-1,3,6,9-tetraazaspiro [4.4]-nonane, melting at 246° C.

EXAMPLE 6

2.54 parts by weight, of 1-methyl carbamoyl-2-imidazoline and 7.98 parts by weight, of p-tolyl isocyanate are stirred for 63 hours at 110° C. in 15 parts by weight, of toluene. On cooling, a colourless deposit is precipitated and is filtered off under suction and washed with toluene, giving 3.8 parts by weight, of the parabanic acid derivative: 2,4-dioxo-6-methyl carbamoyl-1,3-di-(4-tolyl)-9-(4-tolyl carbamoyl)-1,3,6,9-tetraazaspiro [4.4]nonane, melting at 254° C.

EXAMPLE 7

1.68 parts by weight, of 4-methyl-2-imidazoline and 12.2 parts by weight, of p-chlorophenyl isocyanate are stirred for 73 hours at 110° C. in 10 parts by weight, of toluene. On cooling, a colourless deposit is precipitated which is filtered off under suction and washed with toluene, giving 12.7 parts by weight, of the parabanic acid derivative: 2,4-dioxo-1,3-bis-(p-chlorophenyl)-6,9-bis-(p-chlorophenyl carbamoyl)-7-methyl-1,3,6,9-tetraaza-spiro [4.4]-nonane, melting at 180° C. IR (KBr): 1787 cm$^{-1}$, 1725 cm$^{-1}$, 1683 cm$^{-1}$ (C=O).

EXAMPLE 8

(a) 3.5 parts by weight of 2-imidazoline and 28.2 parts by weight, of 3,4-dichlorophenyl-isocyanate are stirred for 2 hours at 110° C. in 50 parts by weight, of toluene. On cooling, a colourless deposit is precipitated and is filtered off under suction and washed with cyclohexane, giving 24.0 parts by weight, of the parabanic acid derivative: 1,3-bis-(3,4-dichlorophenyl)-6,9-bis-(3,4-dichlorophenyl carbamoyl)-2,4-dioxo-1,3,6,9-tetraazaspiro [4.4]-nonane, melting at 233°–234° C.

|  |  | C | H | Cl | N |
|---|---|---|---|---|---|
| $C_{31}H_{18}Cl_8N_6O_4$ | Calculated | 45.28 | 2.21 | 34.50 | 10.22 |
| (822.2) | Observed | 45.3 | 2.3 | 34.1 | 10.1 |

(b) 0.1 parts by weight of the compound prepared according to (a) are dissolved in 4.7 parts by weight of acetone. This solution is suspended in 95 parts by weight of water after the addition of 0.3 part by weight polyglycolalkylarylether. This suspension shows a very good effectivity against Fusicladium especially on apple seedlings. The Fusicladium-test is described in various U.S. patent specifications such as U.S. published patent application No. B 407,014 or in the U.S. Pat. No. 3,895,020 and in "Plant pathology" by George N. Agrios, Academic Press (New York).

EXAMPLE 9

0.7 parts by weight, of 2-imidazoline and 5.3 parts by weight, of p-tolyl isocyanate are stirred for 130 hours at 110° C. in 10 parts by weight, of toluene. On cooling a colourless deposit is precipitated which is filtered off under suction and washed with toluene, giving 3.8 parts by weight, of the parabanic acid derivative: 2,4-dioxo-1,3-di-p-tolyl-6,9-di-p-tolyl carbamoyl-1,3,6,9-tetraazaspiro [4.4]-nonane, melting at 248° C.

EXAMPLE 10

1.24 parts by weight, of hexahydrobenzimidazole and 7.52 parts by weight, of 3,4-dichlorophenyl isocyanate are stirred for 25 hours at 130° C. in 10 parts by weight, of chlorobenzene. On cooling, a colourless deposit is precipitated and is filtered off under suction and washed with ether, giving 4.8 parts by weight, of the parabanic acid derivative: 1,3-bis-(3,4-dichlorophenyl)-6,9-bis-(3,4-dichlorophenyl carbamoyl)-2,4-dioxo-1,3,6,9-tetraaza-7,8-tetramethylene-spiro [4.4]-nonane, melting at 246° C.

What we claim is:

1. Parabanic acid aminal of the formula

[Structural formula of parabanic acid aminal with substituents $R^1$, $R^2$, $R^3$, $R^4$, $R^5$]

wherein $R^1$ is hydrogen or $$Z-NH-\underset{\underset{O}{\|}}{C}-$$

wherein Z is selected from the group consisting of alkyl having 1–5 carbon atoms, allyl, dodecyl, oleyl, stearyl, cyclohexyl, chloroethyl, methoxymethyl, cyanopropyl, phenyl, tolyl, benzyl, chlorophenyl, nitrophenyl, cyanophenyl, methoxyphenyl and naphthyl;

$R^2$ and $R^3$ are the same or different and each is selected from the group consisting of hydrogen, methyl, ethyl, cyclohexyl, phenyl, chlorophenyl and naphthyl;

$R^4$ is $$Z-NH-\underset{\underset{O}{\|}}{C}-$$

and $R^5$ is the same as Z.

2. 1,3-dicyclohexyl-6,9-bis-cyclohexyl carbamoyl-2,4-dioxo-1,3,6,9-tetraaza-spiro[4.4]-nonane.

3. 1,3-dimethyl-6,9-bis-methyl carbamoyl-2,4-dioxo-1,3,6,9-tetraaza-spiro[4.4]-nonane.

4. 1,3-diallyl-6,9-bis-allyl-carbamoyl-2,4-dioxo-1,3,6,9-tetraaza-spiro [4.4]-nonane.

5. 2,4-dioxo-1,3-diphenyl-6-phenyl carbamoyl-1,3,6,9-tetraazo-spiro [4.4]-nonane.

6. 2,4-dioxo-6-methyl carbamoyl-1,3-di-(4-tolyl)-9-(4-tolyl carbamoyl)-1,3,6,9-tetraaza-spiro [4.4]-nonane.

7. 2,4-dioxo-1,3-bis(p-chlorophenyl)-6,9-bis-(p-chlorophenyl carbamoyl)-7-methyl-1,3,6,9-tetraaza-spiro [4.4]-nonane.

8. 1,3-bis-(3,4-dichlorophenyl)-6,9-bis-(3,4-dichlorophenyl carbamoyl)-2,4-dioxo-1,3,6,9-tetraaza-spiro [4.4]-nonane.

9. 2,4-dioxo-1,3-di-p-tolyl-6,9-di-p-tolyl carbamoyl-1,3,6,9-tetraaza-spiro [4.4]-nonane.

10. 1,3-bis-(3,4-dichlorophenyl)-6,9-bis-(3,4-dichlorophenyl carbamoyl)-2,4-dioxo-1,3,6,9-tetraaza-7,8-tetramethylene-spiro [4.4]-nonane.

* * * * *